United States Patent [19]
Rosenthal et al.

[11] Patent Number: 4,744,785
[45] Date of Patent: May 17, 1988

[54] AUTOTRANSFUSION SYSTEM

[75] Inventors: Arthur L. Rosenthal, Hopkinton, Mass.; John Uhoch, Warwick; Augustus Felix, Cranston, both of R.I.

[73] Assignee: C. R. Bard, Inc., Murray Hill, N.J.

[21] Appl. No.: 656,955

[22] Filed: Oct. 2, 1984

[51] Int. Cl.$^4$ .............................................. A61M 1/02
[52] U.S. Cl. ........................................ 604/4; 604/319; 604/320; 604/324
[58] Field of Search .................. 604/4, 5, 6, 7, 28, 604/49, 317, 318, 319, 320, 403, 905, 23, 35, 30, 238, 244, 245; 128/325, 764

[56] References Cited
U.S. PATENT DOCUMENTS

| | | | |
|---|---|---|---|
| 3,405,723 | 10/1968 | Jellies | 604/403 X |
| 3,512,806 | 5/1970 | Romney et al. | 604/403 |
| 3,923,065 | 12/1975 | Nozick et al. | 128/325 X |
| 4,245,637 | 1/1981 | Nichols | 604/320 |
| 4,306,557 | 12/1981 | North | 604/319 |
| 4,402,687 | 9/1983 | Denty et al. | 604/319 |
| 4,430,084 | 2/1984 | Deaton | 604/319 X |
| 4,465,485 | 8/1984 | Kashmer et al. | 604/320 |
| 4,547,186 | 10/1985 | Bartlett | 604/4 |
| 4,564,359 | 1/1986 | Ruhland | 604/4 |
| 4,569,674 | 2/1986 | Phillips et al. | 604/319 |

FOREIGN PATENT DOCUMENTS 82510 6/1983 European Pat. Off. ............ 604/319

*Primary Examiner*—Matthew L. Schneider
*Attorney, Agent, or Firm*—Wolf, Greenfield & Sacks

[57] ABSTRACT

An autotransfusion system for collecting and salvaging blood from a patient's body cavity and for returning it to the patient includes a collection bottle which is detachably connected by an arrangement of ports and an adapter to a source of suction as well as to a conduit from the patient. When the bottle is connected to the system the suction draws the blood into the bottle. When the bottle has been filled and it is desired to return the blood to the patient or for further processing before returning it to the patient the container is easily detached and may be connected to an intravenous delivery set. During reinfusion blood may continue to be collected by the system by replacing the original container with another container. The system may be operated by suction from commonly available fittings in hospital environments or may be connected to a thoracic drainage system to utilize the suction from that system to operate the autotransfusion device. The system may be formed from molded plastic materials and is adapted for disposable one-time use.

17 Claims, 3 Drawing Sheets

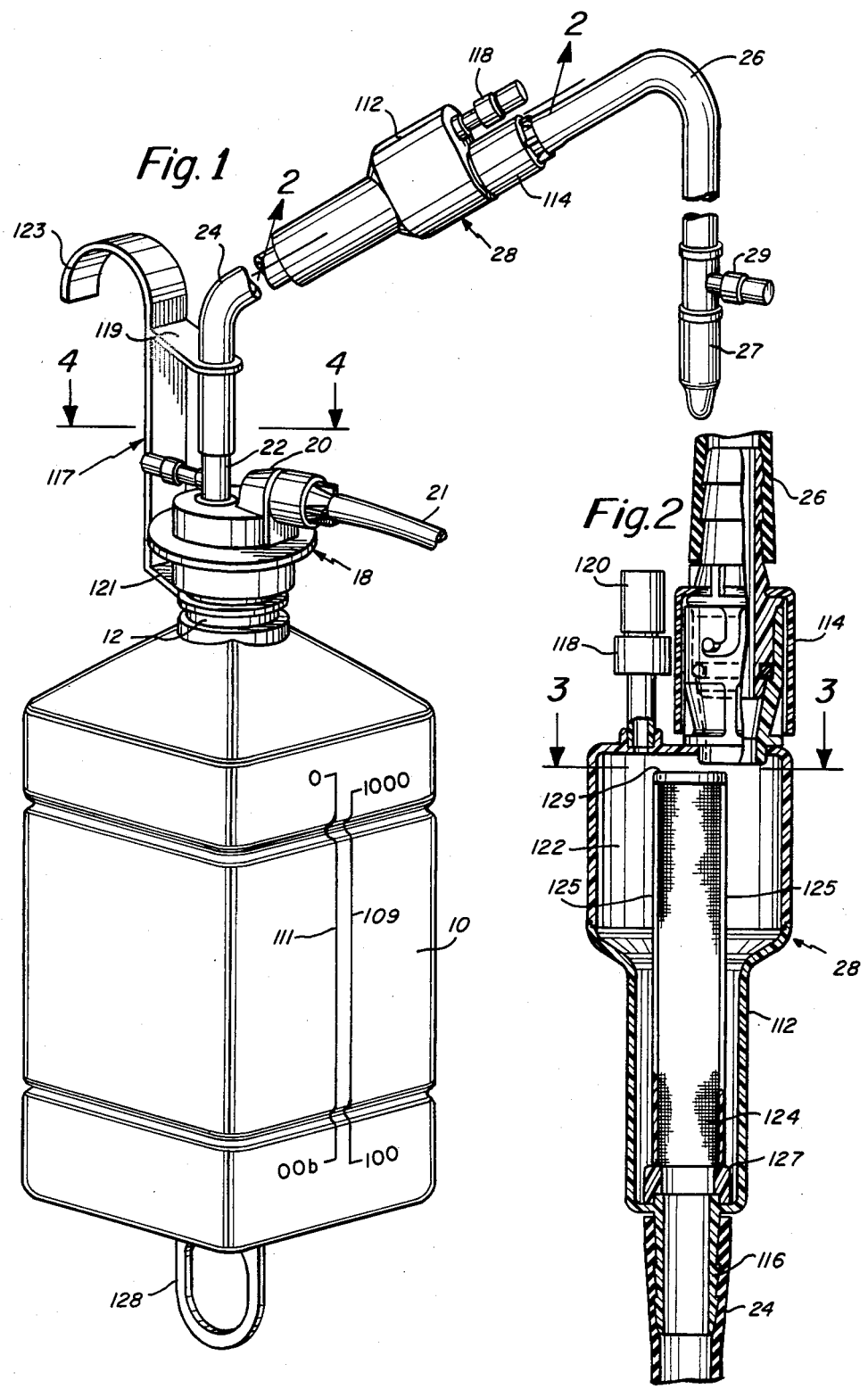

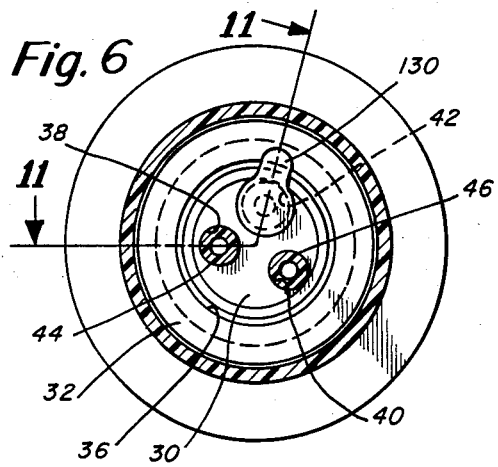
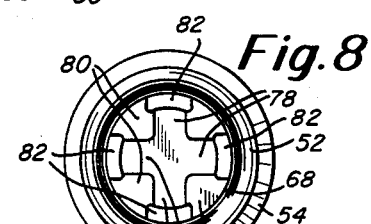
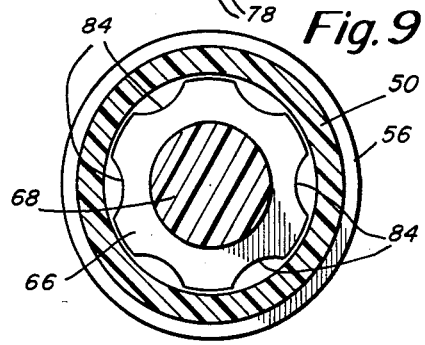
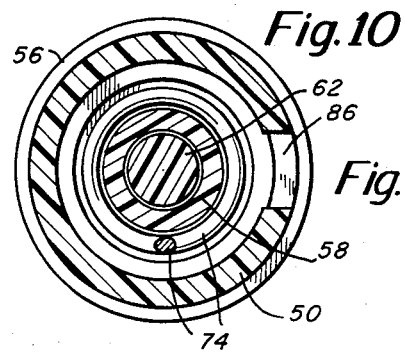
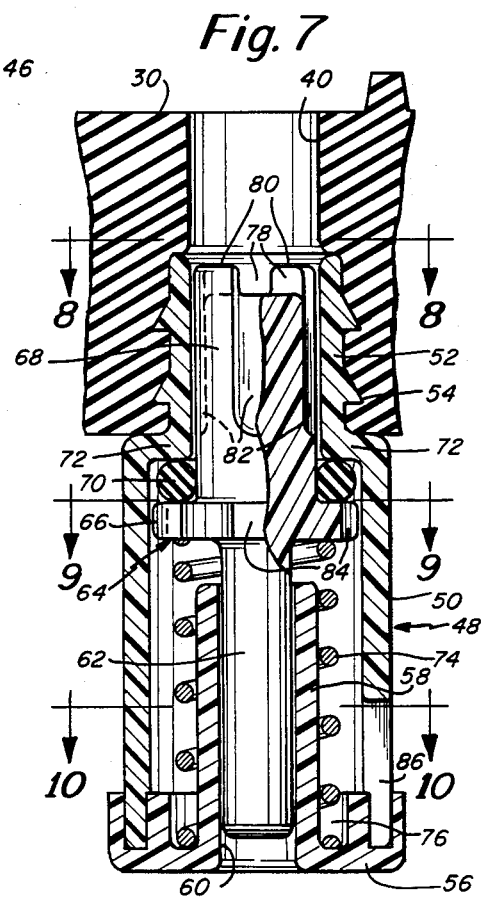
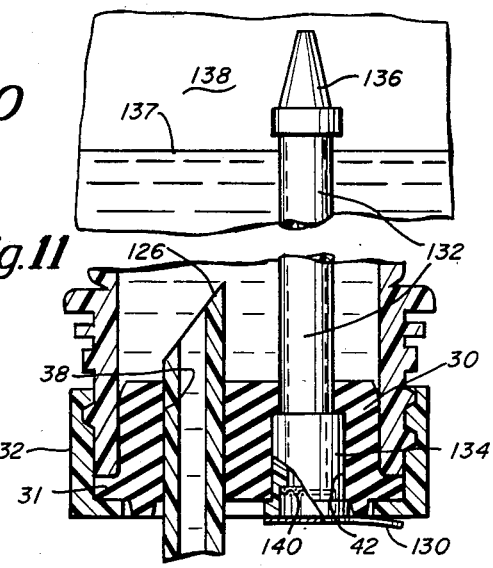

AUTOTRANSFUSION SYSTEM

FIELD OF THE INVENTION

This invention relates to autotransfusion systems for collection and salvaging of blood which pools within a body cavity such as the thoracic or abdominal cavity as a result of surgery.

BACKGROUND OF THE INVENTION

Autotransfusion involves a procedure in which a patient's blood which collects in a body cavity such as the thoracic or abdominal cavity, may be drained from that cavity, salvaged and reinfused into the patient's blood system. The blood may be returned directly to the patient or may be processed before being returned. Autotransfusion provides a number of advantages in patient care. An important advantage is that by returning the patient's own blood to his circulatory system the need for transfusion of blood from donors is reduced and in some instances may even be avoided. Reinfusion of the patient's own blood is very desirable because it reduces the risk of infection or other hematological complications which may result from the patient receiving blood transfusions from donors. Cross-matching and blood typing is minimized or eliminated. The invention provides an improved, disposable and easy to use autotransfusion system.

SUMMARY OF THE INVENTION

The system includes a collection bottle having a stopper assembly secured at the container mouth. The stopper assembly is detachably connectable to an adapter which, in turn, is connected to drainage tubing leading from the patient as well as to a suction source. The stopper assembly has a number of ports which receive an arrangement of spikes on the adapter insertable into the ports in the stopper assembly. The stopper assembly also has a valved air inlet and filtering means to enable filtered air to be admitted into the container during reinfusion.

The adapter has one fitting for connection to a source of suction and another fitting for connection to the drainage tube which leads from the patient's cavity from which the blood is to be collected. The system also includes a blood filter arrangement in the inlet conduit to remove blood clots.

The stopper assembly includes three ports. One of the ports receives an inlet spike on the adapter. The inlet spike is in communication with the tube from the patient. Another port in the stopper assembly receives the suction spike of the adapter, the suction spike being in communication with the suction source. The suction port in the stopper assembly includes a normally closed one-way valve which is opened in response to insertion of the suction spike into that port. A third port in the stopper assembly receives an air inlet tube which extends nearly to the bottom of the container. When the container is inverted to reinfuse the blood into the patient, the end of the inlet tube is above the liquid level to direct air directly to the space above the blood. The end of the air inlet tube has a one-way valve to prevent blood from entering the tube. The stopper assembly also has a bacteriological filter and a seal which must be removed manually in order to expose air inlet port. When the seal is removed the filtered port provides an aseptic means to permit air to be drawn into the collection bottle as the blood flows from the bottle to the patient.

The system may be used with conventionally available sources of suction as are commonly available in operating and recovery rooms as well as in hospital patient rooms. The system also is intended to be used in conjunction with thoracic cavity drainage devices, for example, of the type described in U.S. patent application Ser. No. 626,434, filed June 29, 1984, which may be suction operated devices. Thus the present invention is intended to be compatible with such thoracic collection devices and may be connected to and operated by the suction in the patient tube of such a device.

It is among the general objects of the invention to provide an improved and easy to use autotransfusion system.

Another object of the invention is to provide an autotransfusion which is inexpensive and which lends itself to disposable one-time use.

Another object of the invention is to provide an autotransfusion system of the type described in which the components of the system are quickly and easily connected or detached from each other.

A further object of the invention is to provide an autotransfusion system in which collection of blood may proceed simultaneously with reinfusion of collected blood.

DESCRIPTION OF THE DRAWINGS

The foregoing and other objects and advantages of the invention will be appreciated more fully from the following further description thereof, with reference to the accompanying drawings wherein:

FIG. 1 is an illustration of the collection container, stopper assembly, adapter, blood filter and related tubing which form the system;

FIG. 2 is a sectional illustration of the blood filter as seen along the line 2—2 of FIG. 1;

FIG. 6 is a sectional illustration of the stopper assembly and adapter as seen along the line 6—6 of FIG. 5;

FIG. 7 is an enlarged sectional elevation of the one-way valve assembly in the suction port of the stopper assembly;

FIG. 8 is a plan view of the upper end of the one-way valve as seen along the line 8—8 of FIG. 7;

FIG. 9 is a sectional illustration of the one-way valve as seen along the line 9—9 of FIG. 7;

FIG. 10 is a sectional illustration of the one-way valve as seen along the line 10—10 of FIG. 7; and FIG. 11 is a sectional and fragmented illustration of the container when in an inverted position to reinfuse blood to the patient, as seen along the line 11—11 of FIG. 6.

DESCRIPTION OF THE PREFERRED EMBODIMENT

Figure 3:
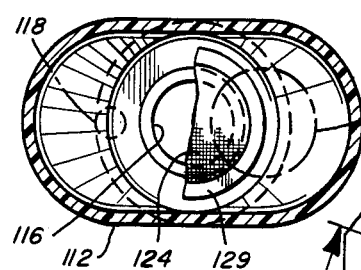
FIG. 3 is a sectional illustration of the blood filter as seen along the line 3—3 of FIG. 2.

As shown in FIG. 1 the system includes a collection container 10 which may be molded from an appropriate plastic material. The container 10 is formed to include a neck 12 which defines the opening to the container. A stopper assembly 14 (see FIG. 5) fits within the container opening 16 defined by the neck 12. A suction and flow adapter 18 is detachably connectable to the stopper assembly 14. The adapter 18 includes a suction fitting 20 which is connectable to a source of suction, indicated generally at tube 21, and which may be the inlet tube 21 of a thoracic drainage device. The adapter 18 also has an inlet fitting 22 which is connectable to the drainage conduit 24, 26 which carries blood from the patient. The drainage conduit 26 has a fitting 27 at its end to enable it to be connected to the drainage tube, such as a thoracotomy tube, which leads directly from the patient's cavity which is to be drained.

The system also includes a blood filter indicated generally at 28, which is located in the conduit 24, 26. The system may be provided with injection ports 29 at locations where it may be desirable to have the capability to inject anticoagulant or other liquids. The injection ports 29 are provided with a self-sealing rubber septum 31 to provide sealed access by a syringed needle. An injection port 29 may be provided, for example, at the inlet to the container as by locating a port 29 at the inlet fitting 22 of the adapter 18. Another injection port 29 may be provided at the proximal end of the conduit 26.

Figure 5:
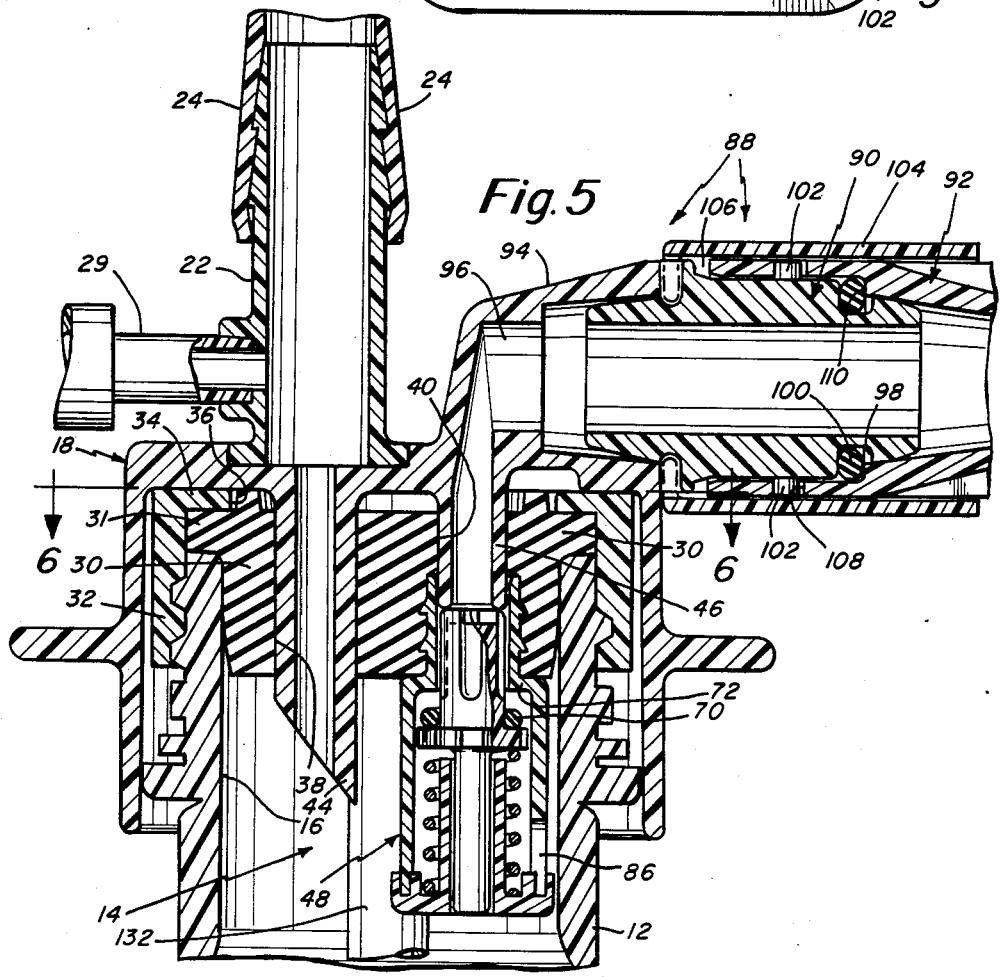
FIG. 5 is a sectional illustration of the assembled stopper assembly and adapter as seen along the line 5—5 of FIG. 4.

As shown in FIG. 5 the stopper assembly 14 includes a stopper 30 which may be formed from an elastomeric material. The stopper 30 has a peripheral flange 31 which rests on the upper edge of the neck 12 and is secured in place in sealed relation on the neck 12 of the container 10 by a retention collar 32 which is threaded onto the neck 12. The retention collar 32 has a top wall 34 with an enlarged central circular opening 36 through which the top surface of the stopper 36 is exposed (see FIG. 6). The stopper has three ports including an inlet port 38, a suction port 40 and a venting port 42. The inlet port 38 and suction port 40 are arranged to receive an inlet spike 44 and a suction spike 46, respectively, which are formed integrally with and extend downwardly from the adapter 18. As shown in FIG. 6 the inlet port 38 and suction port 40 of the stopper 30 are arranged asymmetrically with the inlet and suction spikes 44, 46 being similarly arranged. The asymmetrical arrangement of the ports and spikes assures that the adapter 18 can be connected to the stopper only in the predetermined and correct orientation. The inlet spike 44 is in communication with the inlet conduit 24, 26 and the suction spike 46 is in communication with a source of suction.

The suction port 40 is maintained in a closed, sealed configuration when the stopper assembly is detached from the adapter module 18 by means of a one-way valve assembly 48 which is mounted to the stopper 30 in communication with suction port 40. The valve assembly 48 extends downwardly so that it will be located interiorally of the container 10 as shown in FIG. 5. The valve assembly 48 serves to close off and seal the port 40 at all times except when the spike 44 is in place. The valve 48 prevents blood from leaking out of the container 10 when the container 10 is inverted during reinfusion. The valve assembly 48 is actuated by the suction spike 44 when the spike 44 is inserted into the suction port 40 of the stopper 30. Insertion of the suction spike 46 into the suction port 40 shifts the valve assembly 48 to an open configuration to commumunicate the interior of the container 10 with the source of suction to promote drawing of blood through the system and into the collection container 10.

As shown in further detail in FIGS. 7–10 the valve assembly 48 includes a cylindrical housing 50 which has a neck 52 at its upper end with a number of barbed rings 54 to hold the neck securely within the suction port 40. The lower end of the housing 50 preferably is capped by an end cap 56. The end cap has a central, upwardly extending sleeve 58 having a central bore 60. The bore 60 is arranged to receive a guide end 62 of an axially movable valve member 64. The valve member 64 includes an enlarged flange 66 about its mid-portion and a valve stem 68 which protrudes upwardly into the neck 52 of the valve housing 50. An O-ring 70 which is carried by the valve member 64 serves as one of the sealing elements for the valve. The O-ring 70 rests on the upper surface of the flange 66 and surrounds the valve stem 68. The flange 66 and O-ring 70 are arranged so that the O-ring is in alignment with an annular shoulder 72 formed integrally with the housing 50 at the transition of the main portion of the housing with the neck 52.

The valve member 64 is biased in an upward direction as seen in FIG. 7, to seal the O-ring 70 against the shoulder 72, by a compression spring 74. The compression spring 74 fits over the sleeve 58 of the end cap 56 with the lower end of the spring 74 being received and retained within an annular socket 76 in the end cap 56. The upper end of the compression spring 74 bears against the underside of the flange 66.

The upper end of the valve stem 68 is castellated to define cross-flow channels 78 (see FIG. 8). The cross-flow channels 78 are separated and defined by a plurality of pads 80 against which the lower end of the suction spike 46 can bear. The cross-flow channels 78 communicate with vertically extending flow channels 82 which extend peripherally and downwardly about the outer surface of the valve stem 68. When the suction spike 46 is in engagement with the upper end of the valve stem 68, as shown in FIG. 5, flow communication is established through the spike 46 and downwardly along the periphery of the valve stem 68 via the cross-flow channels 78 and vertical channels 82. Communication is established with the interior of the container 10 by means of a plurality of circumferentially spaced openings 84 in the flange 66 and an aperture 86 in the lower end of the housing 50. Thus, when the adapter 18 is attached to the stopper assembly 14, the suction spike 46 will be inserted into the suction port 40 to engage the stem 68 and urge the valve member 64 downwardly to an open configuration. Conversely, when the suction spike 46 is removed, the spring 74 will urge the valve member 66 to a sealed configuration in which the O-ring 70 is sealingly engaged with the shoulder 72 on the housing 50.

The valve assembly 48 is oriented with respect to the inlet port 38 to avoid the chance of blood flowing in through the inlet spike 44 from becoming immediately ingested into the suction system. That is avoided by orienting the valve 48 so that its opening 86 faces away from the outlet end of the inlet spike 44. As can be seen from FIG. 5 the valve opening 86 faces the neck 12 of the container, away from the outlet end of spike 44 thereby assuring that no inlet blood will be drawn into the suction conduit to the valve 48.

In accordance with the invention the system employs quick disconnect fittings to facilitate rapid and easy connection and disconnection of the various tubes and fittings in the system. FIG. 5 illustrates a preferred construction for the quick disconnect fitting. The quick disconnect fitting, indicated generally at 88, includes a male section 90 and female section 92. In the embodiment shown in FIG. 5 the male section 90 is secured, as by adhesive or the like, to a portion 94 of the adapter 18 which defines a channel 96 in communication with the suction spike 46. The male section 90 projects outwardly from the adapter portion 94. The outwardly projecting end of the male section 90 has a circumferential groove 98 which receives and retains an O-ring 100. The male section 90 also is provided with a pair of bayonet pins 102.

The male section 90 preferably is enclosed with an enlarged cylindrical sleeve 104 which extends distally beyond the outer end of the male section 90 to enclose fully the male section 90. The outer diameter of the sleeve 104 is spaced from the outer diameter of the male section 90 to define an annular space 106 in which the female section 92 of the connector may be received. The sleeve serves to prevent direct contact of the protruding end of the male section 90 to reduce the chances of it becoming contaminated.

Figure 4:
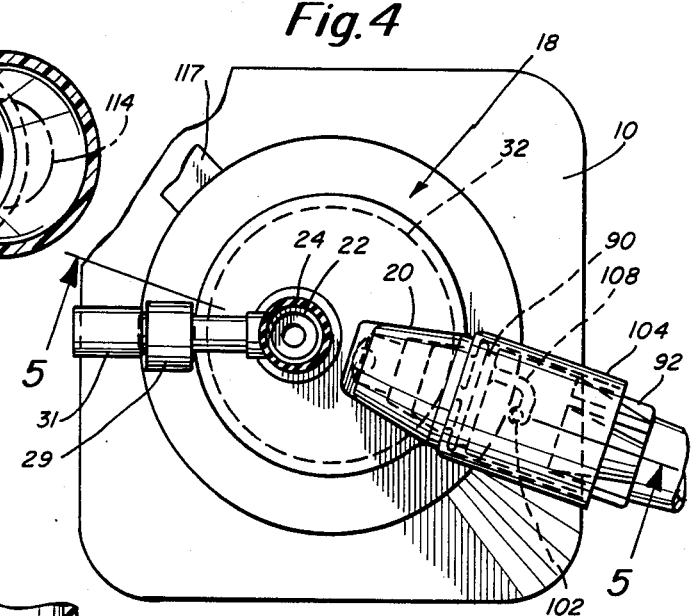
FIG. 4 is a plan view, partly in section, of the collection container and adapter as seen along the line 4—4 of FIG. 1.

As shown in FIGS. 4 and 5 the female section 92 of the connector is provided with a pair of L-shaped bayonet slots 108 to receive the bayonet pins 102 on the male section 90. The female section 92 also is formed with a shoulder 110 which will engage the O-ring 110 when the bayonet connection is secured. The O-ring 110 also may be of a diameter large enough so that it will snugly and sealingly engage the inner cylindrical surface of the female section 92. Thus, with the quick disconnect arrangement illustrated in FIG. 5, the female section 92 which is attached to the tube leading to the suction source can be quickly and easily disconnected or reconnected as desired.

The system also includes a blood filter 28, shown in FIGS. 1 and 2, which is located in the inlet conduit 24, 26 extending from the patient to the collection container 10. The blood filter 28 includes a housing 112 which may be molded from plastic. The filter has a quick disconnect fitting 114 at the inlet end and an outlet nipple 116 at the other end, the outlet nipple 116 being connected to conduit 24 and the inlet being connected to conduit 26. The housing 112 also may include an injection port 118 having a self-sealing rubber septum 120 to facilitate injection of anticoagulant or other liquids as well as to permit sampling of blood from the filter chamber 122. Blood filter 28 has a filter element 124 which may be mounted within the chamber 122 to the outlet end of the filter housing 112. As shown in FIG. 2 the filter element 124 may be of elongate tubular configuration. It may be formed from polyester having interstices of the order of 265 microns. The tubular filter element 124 may be supported by a plastic frame which is secured within the housing 112. The frame may include a pair of elongate side supports 125 secured to a base 127 which, in turn, is attached to the interior of the housing 112 at the outlet end. The upper end of the side supports 125 may be secured to each other and to the upper end of the filter element 124 by a top member 129.

The system may be connected directly to the central suction system commonly found in hospitals. The suction fitting may be connected as by tube 21 to the suction source. Fitting 27 of conduit 22 may be connected to a thoracotomy tube or similar tube extending from the patient. The system also is easily and directly connectable to thoracic drainage systems such as those described in the aforementioned patent application Ser. No. 626,434. Thus, where a thoracic drainage device already is attached to the patient it is not necessary to insert additional tubes into the patient in order to use the present invention. The inlet from the thoracic drainage device need only be disconnected from the tube leading from the patient to permit the present autotransfusion device to be inserted in line between the drainage device and the patient tube. Thus, the inlet tube 21 to the thoracic drainage device can serve as the source of suction and the inlet fitting 27 to the device may be connected directly to the tube leading from the patient. After the autotransfusion system is no longer to be used it can be removed simply and easily from between the patient tube and drainage device. The drainage device then can be reconnected directly to the patient tube and its operation can be resumed independently of the autotransfusion system.

In order to conveniently mount the system at the patient's bedside during collection, a hanging hook 123 is provided. The hook may be formed from plastic or of wire. The hanger 117 includes an upper arm 119 and a lower arm 121 which clip onto the tube 24 and neck 12 respectively. The arms 119, 121 are provided with snapon C-shaped collars at their distal ends to snap fit onto the system. Hanger 117 includes an integrally formed hook 123 at its upper end by which the device may be hung from the bedrail.

When it is desired to reinfuse the collected blood or to deliver the blood for further processing before reinfusion, the collection container 10 is detached from the adapter 18. It may be replaced with another container if the autotransfusion device is to remain in place if collection is to continue. In order to reinfuse the collected blood in the patient the container 10 is connected to a conventional intravenous delivery set having an intravenous needle at one end and a connection spike 126 in the other end. As shown in FIG. 11 the spike 126 from the proximal end of the intravenous delivery set is inserted into the inlet port 38. The container 10 then is hung in an inverted elevated position to enable the blood to gravitate through the intravenous tubing to the patient. A hanging tab or hook 128 may be mounted on or molded integrally with the bottom of the container for that purpose (FIG. 1).

The container 10 is provided with a pair of volumetric scales 109, 111 which are inverted with respect to each other. Scale 109 thus provides an indication of the volume of blood which has been collected during the collection phase. Scale 111 is for use during reinfusion and provides an indication of the volume of blood remaining in the container 10.

In order to enable the blood to flow from the container 10, the venting port 42 in the stopper 30 must be open. Thus, when it is desired to reinfuse the collected blood, the tab 130 is simply and easily removed. The venting arrangement includes an elongate vent tube 132 which is attached by a collar 134 to the stopper 30 at the vent port 42. The collar 134 fits snugly within the vent port 42. The vent tube 132 extends downwardly toward the bottom of the container and has, at its free end, a one-way duckbill valve 136. The duckbill valve 136 is normally closed but will permit air to flow through the tube 132 into the container. The elongated vent tube 132 and duckbill valve 136 insure that no blood will enter the vent tube 132 as the container is inverted from its collecting to its reinfusion positions. The vent tube 132 is sufficiently long so that when the container is inverted the free surface surface 137 of the blood will be below the duckbill valve 136 to assure that the valve will communicate directly with the space 138 above the plug 136. The collar 134 is provided with an internally mounted filter to filter the air so as to prevent entry of contaminants to the container during reinfusion. Preferably the filter 140 will have a pore size of the order of 0.45 micron and will be a reinforced hydrophobic membrane. Filters of this type are available commercially. The venting port normally is sealed by a removable seal which may be a strip of flexible plastic in the form of a tab 130 (see FIG. 6) attached to cover the venting port 42. The tab 130 preferably is formed from a thermoplastic material which can be heat sealed directly to the collar 134 which also is formed from a thermoplastic material. Alternately, the removable seal may be attached by adhesives.

From the foregoing it will be appreciated that we have provided a simple, easily used and inexpensive autotransfusion system. The system may be fabricated from relatively lowcost plastic molded parts and is adapted so that it may be used once and then discarded. The system does not require that the blood collection process be stopped during reinfusion and enables both procedures to be performed simultaneously. Additionally, the system can be used easily in conjunction with thoracic cavity drainage systems or with conventionally available hospital suction systems. It should be understood, however, that the foregoing description of the invention is intended merely to be illustrative thereof and that other embodiments and modifications may be apparent to those skilled in the art without departing from its spirit.

Having thus described the invention what we desire to claim and secure by Letters Patent is:

1. An autotransfusion system for the collection and reinfusion of blood comprising:
    a collection container;
    flow port means to enable blood to flow into and from the container;
    suction port means in communication with the container to enable the container to be connected to a source of suction;
    valve means associated with the suction port for normally closing the suction port means, said valve means being openable in response to connection of a source of suction with the suction port; and
    vent means associated with the container to permit venting of the container while collected liquid is permitted to flow out of the container through said flow port means.

2. An autotransfusion system as defined in claim 1 further comprising:
    the container having an opening therein;
    a stopper disposed in the opening;
    each of said flow port means, suction port means and vent means being formed in the stopper;
    an adapter having a fluid flow passage and a suction passage for connection with said port means in the stopper; and
    registration means for precluding connection of the adapter with the stopper except in a predetermined configuration.

3. An autotransfusion system as defined in claim 2 wherein said registration means comprises:
    said flow port means and suction port means being arranged asymmetrically on said stopper;
    said adapter having spikes defining said fluid flow passage and suction passage, the spikes being arranged on the adapter asymmetrically in a configuration to mate with the asymmetrically disposed port means on the stopper.

4. An autotransfusion system as defined in claim 1 further comprising:
    an adapter detachably connectable to the container, the adapter having an inlet port connectable to the flow port means and being connectable to a a first conduit for carrying blood to the container, the adapter further having a passage connectable to a second conduit communicating the container with the source of suction, said adapter being detachably connectable to said container in a manner in which the first conduit communicates with the flow port means and second conduit communicates with the suction port means.

5. An autotransfusion system as defined in claim 4 further comprising:
    registration means for precluding connection of the adapter with the container except in a configuration in which the first conduit is in communication with the flow port means and the second conduit is in communication with the suction port means.

6. An autotransfusion system as defined in claim 5 further comprising:
    said inlet port and passage on the adapter comprising spikes adapted to extend into the flow port means and suction port means respectively.

7. An autotransfusion system as defined in claim 6 wherein said valve means further comprises:
    a normally closed valve mounted in the suction port means, the valve having an actuating member accessible through the suction port means and being located as to be engageable with the suction spike on the adapter when the adapter is connected to the container;
    means normally biasing the valve means in a closed position when the suction spike is withdrawn from the suction port means.

8. An autotransfusion system as defined in claim 7 further comprising:
    said valve means having a flow port in communication with the interior of the container, said valve means, flow port and flow port means being constructed and arranged to prevent blood from flowing from the flow port means to the suction opening in the valve means.

9. An autotransfusion system as defined in claim 4 further comprising:
    blood filter means for filtering blood disposed exteriorally of the collection container and having an outlet connectable to the inlet port of the adapter, the blood filter means having an inlet end detachably connectable to a blood flow conduit adapted to carry blood from the patient.

10. An autotransfusion system as defined in claim 9 further comprising:
    the inlet to the blood filter having a quick disconnect fitting adapted to be quickly connected to or disconnected from the blood conduit;
    the suction fitting for the adapter having a quick disconnect connector for quickly detaching the adapter from the suction source whereby the system may be quickly disengaged from the patient.

11. An autotransfusion system as defined in claim 1 wherein the vent means comprises:
    a vent tube having one end in communication with the exterior of the container and the other end extending interiorly of the container toward and adjacent to the bottom of the container;

one-way valve means at the end of the vent tube to enable air to flow into the container but to prevent flow of blood outwardly through the vent tube;

a seal for the vent means normally preventing communication between the vent means and the exterior of the bottle.

12. An autotransfusion system as defined in claim 11 wherein said seal is manually disruptable.

13. An autotransfusion system as defined in claim 11 further comprising:

filter means disposed within the vent passage to filter air flow through the vent passage.

14. An autotransfusion system as defined in claim 1 further comprising:

said flow port means, suction port means, valve means and vent means being disposed at the upper end of the container;

means for suspending the container in an upright position; and means for suspending the container in an inverted position.

15. An autotransfusion system as defined in claim 14 wherein said means for suspending the container in said positions further comprises:

a detachably connectable clip at the upper end of the container, the clip being detachably connectable to portions of the upper end of the container;

means for supporting the container in an inverted position comprising hanger means secured to the bottom end of the container.

16. An autotransfusion system as defined in claim 1 further comprising blood filter means disposed exteriorly of the collection container and having an outlet connectable to the inlet port of the adapter, the blood filter having an inlet end detachably connectable to a blood flow conduit adapted to carry blood from the patient.

17. An autotransfusion system as defined in claim 16 further comprising:

the inlet to the blood filter having a quick disconnect fitting adapted to be quickly connected to or disconnected from the blood conduit;

the suction fitting for the adapter having a quick disconnect connector for quickly detaching the adapter from the suction source whereby the system may be quickly disengaged from the patient.

* * * * *